(12) United States Patent
Domankevitz et al.

(10) Patent No.: US 8,328,795 B2
(45) Date of Patent: Dec. 11, 2012

(54) SKIN RESURFACING AT 1930 NM

(75) Inventors: Yacov Domankevitz, Newton, MA (US); Christopher J. Jones, Leicester, MA (US); James C. Hsia, Weston, MA (US)

(73) Assignee: Candela Corporation, Wayland, MA (US)

( * ) Notice: Subject to any disclaimer, the term of this patent is extended or adjusted under 35 U.S.C. 154(b) by 337 days.

(21) Appl. No.: 12/754,374

(22) Filed: Apr. 5, 2010

(65) Prior Publication Data

US 2010/0256617 A1    Oct. 7, 2010

Related U.S. Application Data

(60) Provisional application No. 61/166,582, filed on Apr. 3, 2009.

(51) Int. Cl.
*A61B 18/18* (2006.01)
(52) U.S. Cl. .......... 606/9; 606/2; 607/89; 607/88; 128/898
(58) Field of Classification Search .......... 606/9, 2; 607/89, 88; 128/898
See application file for complete search history.

(56) References Cited

U.S. PATENT DOCUMENTS

| | | |
|---|---|---|
| 5,810,801 A | 9/1998 | Anderson et al. |
| 6,997,923 B2 | 2/2006 | Anderson et al. |
| 2001/0001118 A1 | 5/2001 | Asah et al. |
| 2004/0005349 A1 | 1/2004 | Neev |
| 2005/0215987 A1 | 9/2005 | Slatkine |
| 2006/0259102 A1 | 11/2006 | Slatkine |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0264626 A1 * | 11/2007 | DeBenedictis et al. .......... 435/4 |
| 2008/0015556 A1 * | 1/2008 | Chan et al. .......... 606/9 |
| 2008/0091179 A1 * | 4/2008 | Durkin et al. .......... 606/9 |
| 2008/0215039 A1 | 9/2008 | Slatkine et al. |
| 2009/0069741 A1 * | 3/2009 | Altshuler et al. .......... 604/22 |
| 2009/0137996 A1 | 5/2009 | DeBenedictis |
| 2009/0275879 A1 | 11/2009 | Deem et al. |
| 2009/0275899 A1 | 11/2009 | Deem et al. |
| 2010/0010420 A1 | 1/2010 | Deem et al. |

FOREIGN PATENT DOCUMENTS

| | | |
|---|---|---|
| EP | 1 702 578 | 9/2006 |
| WO | 2008/009005 A2 | 1/2008 |

OTHER PUBLICATIONS

"What is Pearl," Pearl Cutera, http://www.cutera.com/pearl/patients/whatispearl.asp, dated Mar. 21, 2009, 1 page.
International Search Report for PCT/US10/29974 dated Jul. 23, 2010 (5 pages).
Solta Medical, Solta Medical Launches New Fraxel re: Store Dual Laser System, www.solta.com/PressRelease_13.cfm, Aug. 26, 2009, (1 page).

* cited by examiner

*Primary Examiner* — Kinam Park
(74) *Attorney, Agent, or Firm* — Proskauer Rose LLP

(57) ABSTRACT

Non-ablative skin resurfacing can include generating electromagnetic radiation having a wavelength of about 1920 nm to about 1950 nm and a fluence of about 3 $J/cm^2$ to about 6 $J/cm^2$. The electromagnetic radiation is delivered to a target region of skin to cause thermal injury to the epidermis in the target region sufficient to elicit a healing response that produces a substantially improved skin condition without detachment of the epidermis (e.g., within 3 days of treatment).

29 Claims, 10 Drawing Sheets

SKIN RESURFACING AT 1930 NM

CROSS REFERENCE TO RELATED APPLICATIONS

This application claims the benefit of and priority to U.S. Provisional Application Ser. No. 61/166,582 filed Apr. 3, 2009, which is owned by the assignee of the instant application and the disclosure of which is incorporated herein by reference in its entirety.

FIELD OF THE INVENTION

The invention relates generally to skin resurfacing (e.g., improving skin texture and wrinkles) at about 1930 nm, and more particularly to causing thermal injury in the epidermal and/or dermal region of the skin sufficient to elicit a healing response that produces a substantially improved skin condition, while leaving the epidermis substantially intact, at about 1930 nm.

BACKGROUND OF THE INVENTION $CO_2$ and Er:YAG laser systems can be used for ablative skin resurfacing. The ablative $CO_2$ and Er:YAG technologies promote epidermal regeneration and collagen remodeling by removal of the epidermis accompanied by dermal contraction and remodeling. The $CO_2$ laser produces thermal damage extending from 70 to 180 um into the dermis. However, because of high morbidity, significant down time and prolonged recovery period, they have decreased in popularity.

Non-ablative procedures were developed to minimize adverse effect and down time. These technologies protect the epidermis from laser induced thermal injury and leave the outer skin layer intact, typically through aggressive skin cooling. Thermal injury occurs at the deeper dermal structures to induce a wound healing process and remodeling. For example, the 1540 nm wavelength Er:Glass laser produces a mean depth of injury of about 700 µm. However, some patients want more noticeable results with fewer treatments.

SUMMARY OF THE INVENTION

The invention, in one embodiment, features skin resurfacing (e.g., improving skin texture and wrinkles) at about 1930 nm. A treatment can cause thermal injury in the epidermal and/or dermal region of the skin sufficient to elicit a healing response that produces a substantially improved skin condition, while leaving the epidermis substantially intact. In certain embodiments, only the epidermis is damaged (full thickness damage or only a portion of the epidermis). In certain embodiments, the full thickness of the epidermis and an upper portion of the dermis are damaged. In certain embodiments, a portion of the epidermis and an upper portion of the dermis are damaged. The skin resurfacing is non-ablative.

The 1930 nm wavelength is substantially absorbed by water in the epidermis or dermis. A treatment can match or substantially match the penetration depth of the light to the thickness of the epidermis. The 1930 nm wavelength is absorbed by skin more strongly than non-ablative wavelengths and less strongly than ablative wavelengths. The 1930 nm wavelength penetrates shallower than typical non-ablative wavelengths and deeper than ablative wavelengths. As a result, a treatment using 1930 nm can substantially volumetrically heat the whole layer thickness of the epidermis, which can not be achieved at longer or shorter wavelengths. Ablative wavelengths that heat to the same depth as the 1930 nm wavelength result in unwanted ablation of the skin. Non-ablative wavelengths are focused below the epidermis.

The treatment need not immediately ablate the skin. The treatment can leave the skin intact for up to 3 days before the skin begins to desquamate. The treatment can leave the skin intact for at least 3 days before the skin begins to desquamate. In certain embodiments, the treatment leaves the skin intact for up to 7 days before the skin begins to desquamate. Higher fluence treatments result in more immediate desquamation. The treatment can leave the skin intact for at least 6 hours, 12 hours, 18 hours, 1 day, 2 days, 3 days, 4 days, 5 days, 6 days, 7 days, or longer before the skin begins to desquamate. The treatment can cause a thermal damage zone while keeping the epidermis damaged but intact. The damaged intact epidermis can create a natural protective dressing on the skin that remains during the restorative process. This speeds healing time and results in less downtime. An additional advantage of such a treatment is that the treatment can be performed with minimal acute cosmetic disturbance so that the patient can return to normal activity immediately after the treatment.

A treatment can include cooling to protect the skin surface to minimize unwanted injury to the surface of the skin and to minimize any pain that a patient may feel. Cooling, however, is not required. If cooling is used, only superficial cooling is affected so that a portion of the epidermis can be treated. For example, the most superficial layer(s) or portion of the epidermis is cooled, so that it remains intact, while a lower portion of the epidermis is damaged.

Control and specificity of full thickness or substantially full thickness damage of the epidermis has not been previously demonstrated using ablative or non-ablative wavelengths. Furthermore, control and specificity of full thickness or substantially full thickness damage of the epidermis has not been previously disclosed or demonstrated using the 1930 nm wavelength. Non-ablative skin resurfacing at or about 1930 nm has not been demonstrated.

While the use of water as a chromophore, infrared wavelengths and wide ranges of fluences have been suggested for skin resurfacing, previous practitioners have not recognized the unexpected benefits, the effectiveness, or the criticality of matching the damage to the thickness of the epidermis and utilizing 1930 nm for skin resurfacing. Indeed, practitioners have taught against the use of 1930 nm, e.g., suggesting that radiation should be focused in the upper dermis or teaching to ablate the epidermis.

In one aspect, there is a method of non-ablative skin resurfacing. Electromagnetic radiation is generated having a wavelength of about 1920 nm to about 1950 nm and a fluence of about 3 $J/cm^2$ to about 6 $J/cm^2$, and delivered to a target region of skin. Thermal injury is caused to the epidermis in the target region sufficient to elicit a healing response that produces a substantially improved skin condition without detachment of the epidermis.

In another aspect, there is a method of non-ablative skin resurfacing. Electromagnetic radiation is generated having a wavelength of about 1920 nm to about 1950 nm and a fluence of about 3 $J/cm^2$ to about 6 $J/cm^2$, and delivered to a target region of skin. Thermal injury is caused to the epidermis and to the dermis in the target region sufficient to elicit a healing response that produces a substantially improved skin condition without detachment of the epidermis.

In yet another aspect, there is a method of non-ablative skin resurfacing. Electromagnetic radiation is generated having a wavelength of about 1930 nm and a fluence of up to 5 $J/cm^2$, and delivered to a target region of skin. Thermal injury is caused to the epidermis in the target region sufficient to elicit a healing response that produces a substantially improved skin condition without detachment of the epidermis.

In still another aspect, there is a method of non-ablative skin resurfacing. Electromagnetic radiation is generated having a wavelength of about 1920 nm to about 1950 nm, a fluence of about 3 J/cm$^2$ to about 6 J/cm$^2$, and a pulse duration up to 1 second, and delivered to a target region of skin. Thermal injury is caused to the epidermis in the target region sufficient to elicit a healing response that produces a substantially improved skin condition without detachment of the epidermis.

In yet another aspect, there is an apparatus for non-ablative skin resurfacing. The apparatus includes means for generating electromagnetic radiation, e.g., having a wavelength of about 1920 nm to about 1950 nm and a fluence of about 3 J/cm$^2$ to about 6 J/cm$^2$. The apparatus includes means for delivering the electromagnetic radiation to a target region of skin. The apparatus includes means for causing thermal injury to the epidermis in the target region sufficient to elicit a healing response that produces a substantially improved skin condition without detachment of the epidermis. The apparatus can include means for causing cell necrosis to a depth of up to 300 micrometers in the dermis.

In yet another aspect, there is an apparatus including a source generating electromagnetic radiation having a wavelength of about 1920 nm to about 1950 nm and a fluence of about 3 J/cm$^2$ to about 6 J/cm$^2$, and means for receiving the electromagnetic radiation, for absorbing a portion of the electromagnetic radiation to form a plurality of untreated zones, and for transmitting the remaining portion of the electromagnetic radiation to form a region of thermal injury surrounding the plurality of untreated zones. The means for absorbing the electromagnetic radiation can be a mask.

In other embodiments, any of the aspects above, or any apparatus, device or system or method, process or technique described herein, can include one or more of the following features.

Thermal injury can be caused while leaving the epidermis intact for up to 3 days or for up to 7 days. Cell necrosis can be caused to a depth of up to 300 micrometers in the dermis. The epidermis can be left intact for at least 3 days. The treatment can reduce the appearance of wrinkles. Thermal injury can be caused to an upper portion of the dermis in the target region of skin. Thermal injury can be caused without acute cosmetic disturbance to the epidermis. Optical penetration depth of the electromagnetic radiation can be matched to a thickness of the epidermis.

The target region of skin can be exposed to the electromagnetic radiation for up to 1 second. The pulse duration can be less than or equal to 250 milliseconds. The pulse duration can be less than or equal to 50 milliseconds. The wavelength of the electromagnetic radiation can be about 1930 nm or about 1947 nm. A pulsed source or a scanned or gated continuous wave source can be used to generate the electromagnetic radiation. A thulium-doped laser (e.g., thulium:YAP) or a diode laser can be used to generate the electromagnetic radiation. Alternatively, a semiconductor laser or a diode laser can be used to generate the electromagnetic radiation.

In certain embodiments, a pattern of thermal injuries can be formed in the target region of skin. A plurality of thermal injuries can be formed. Each thermal injury can be separated from adjacent thermal injuries by substantially undamaged epidermal tissue. In certain embodiments, a reverse fractional pattern can be formed including regions of undamaged tissue separated from adjacent regions of undamaged tissue by treated epidermal tissue.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

Table 1 shows optical penetration depths for wavelengths commonly used for skin resurfacing (ablative and non-ablative) and for the 1930 nm wavelength.

A treatment can damage the epidermis, which can be about 100 μm±50 μm. The 1930 nm wavelength is advantageous because its optical penetration depth substantially matches the thickness of the epidermis. The treatment can extend into the dermis up to 180 μm, although deeper treatments can be achieved. In certain embodiments, the treatment extends into the dermis by up to 150 μm, up to 100 μm, up to 50 μm, up to 25 μm, up to 10 μm, up to 5 μm, or up to 2 μm.

TABLE 1

Optical penetration depths.

| λ (nm) | $\mu_a$ (cm$^{-1}$) | OPD (μm) |
|---|---|---|
| 10640 | 845 | 12 |
| 2940 | 12202 | 0.8 |
| 2790 | 5882 | 1.7 |
| 1930 | 130 | 77 |
| 1550 | 11 | 909 |
| 1450 | 31 | 323 |

Figure 1:
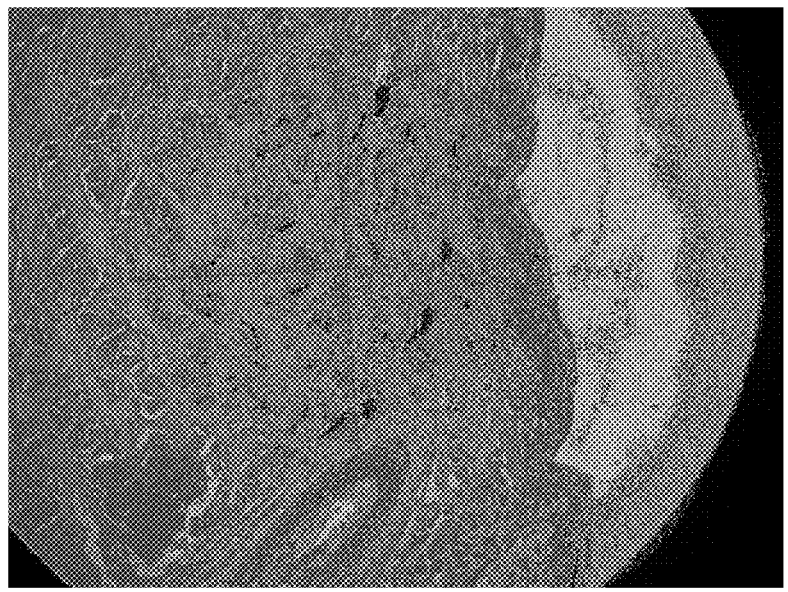
FIG. 1 shows tissue effects from an exemplary tissue experiment.

Tissue experiments were performed on a porcine model. A 16 W 1930±40 nm diode laser system (available from Applied Optronics) delivered energy via a 1.5 mm optical fiber. The pulse duration was up to 1 second. The light was reimaged through an optical lens system to about 3.5-4 mm spot on the skin. FIG. 1 shows the tissue effects resulting from radiant exposure of 5.5 J/cm$^2$, 4 mm spot size and 250 msec pulse duration. The residual thermal damage produced was 100 μm. FIG. 1 also shows that with the 1930 nm laser radiation, the epidermis is thermally denatured but is not removed. An intact epidermis acts as a natural protective dressing, speeds healing, reduces down time, and improves clinical results. Injury of this type can not be achieved using non-ablative or ablative wavelengths. Non-ablative wavelengths result in thermal damage in deeper zones, and ablative wavelengths result in ablation of the epidermis.

Figure 2:
FIG. 2 shows tissue effects from another exemplary tissue experiment.
Figure 3:
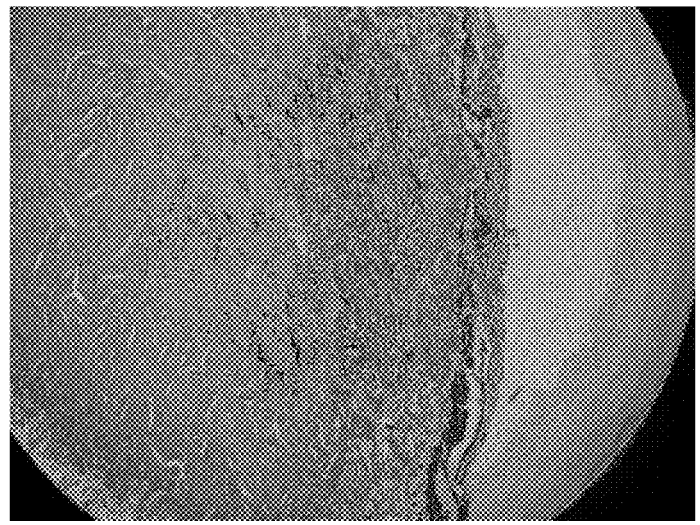
FIG. 3 shows tissue effects from another exemplary tissue experiment.

FIGS. 2 and 3 show that higher fluences or radiant exposures produced deeper zones of residual thermal damage. FIG. 2 shows porcine tissue treated with 8.4 J/cm$^2$, 4 mm spot, 250 msec duration. The residual thermal damage produced is 350 μm. FIG. 3 shows porcine tissue treated with 11 J/cm$^2$, 4 mm spot, 250 msec duration. The residual thermal damage produced is 550 μm. The residual thermal damage zones shown in FIGS. 2 and 3 can create undesired scars or other undesired effects. In FIGS. 2 and 3, the epidermis is shown separating from the dermis.

Tissue experiments were performed on a human subjects. Subjects (skin type I-III) were treated with a 1930 nm diode laser. The pulse duration ranged between 50-150 ms, laser radiant exposure ranged between 3-5.5 J/cm$^2$ at a spot size of 3.5 mm. Skin cooling was not used. Each patient received 1 treatment.

With higher fluences (>5 J/cm$^2$), immediate thermal damage extending as deep as 300 microns without ablation of the epidermis was observed. Pyknosis of nuclei in the epidermis was the earliest sign of damage. Two week and 2 month biopsies showed only mild fibrosis. Mild erythema at lower fluences and slight vesiculation at the higher fluences was observed. No scarring was noted even at sites with early vesiculation.

Figure 4:
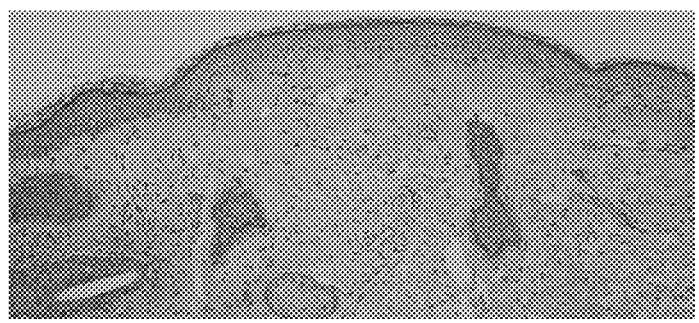
FIG. 4 shows tissue effects from another exemplary tissue experiment.
Figure 5:
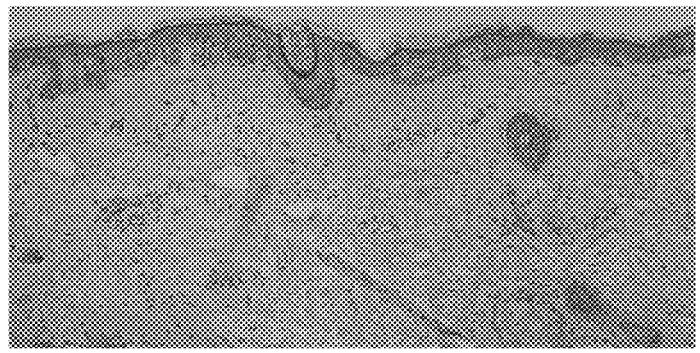
FIG. 5 shows tissue effects from another exemplary tissue experiment.
Figure 6:
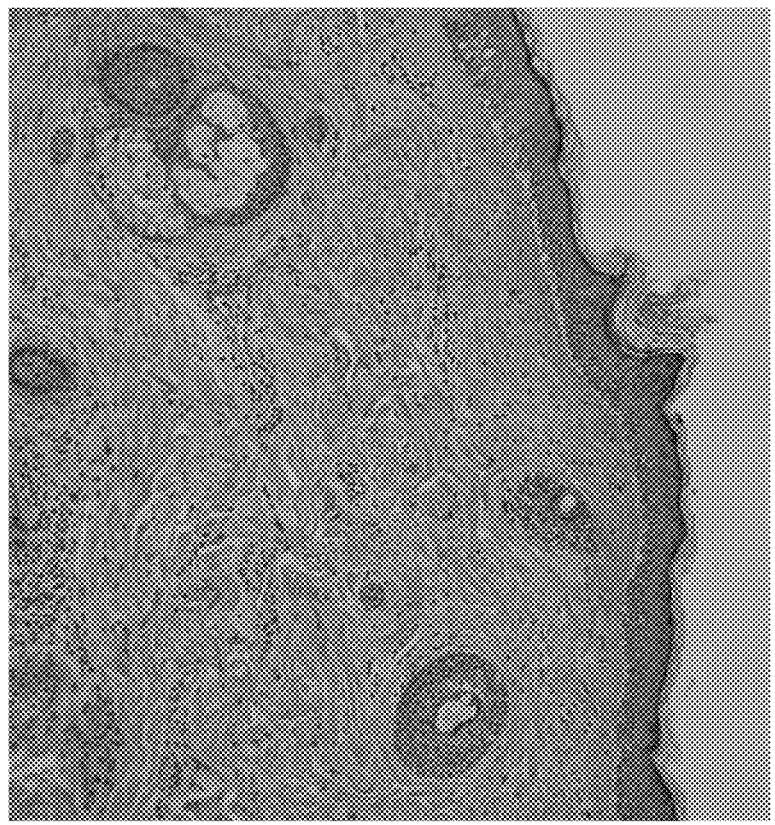
FIG. 6 shows tissue effects from another exemplary tissue experiment.
Figure 7:
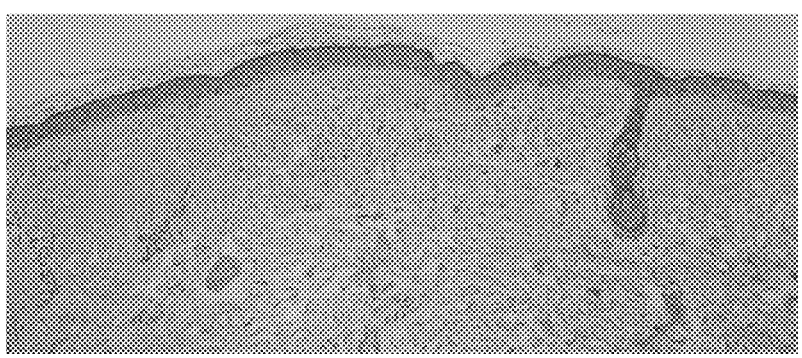
FIG. 7 shows normal skin.

FIG. 4 shows the tissue effects resulting from 3.6 J/cm$^2$, 80 msec at 1930 nm. FIG. 5 shows the tissue effects resulting from 4.2 J/cm$^2$, 80 msec at 1930 nm. FIG. 6 shows the tissue effects resulting from 4.9 J/cm$^2$, 80 msec at 1930 nm. FIG. 7 shows normal skin.

FIGS. 1 and 4-7 show that a relatively narrow window of wavelength, fluence and pulse duration is available for damaging the epidermis without epidermal detachment. The fluence is typically about 3.6 to about 4.9 J/cm$^2$. Full thickness damage of the epidermis can be achieved at 80 milliseconds. Damage to the epidermis and dermis can be achieved at 250 milliseconds. The wavelength can be 1930±40 nm. The spot size can be about 3-5 mm. By varying the input radiant exposure, one can control the effective zone of residual thermal damage and/or confine damage to the epidermis, while leaving it intact.

In various embodiments, a treatment can, for example, improve skin laxity, improve skin texture, tighten skin, strengthen skin, thicken skin, induce new collagen formation, promote fibrosis of skin, partially denature collagen, treat wrinkles, reduce or minimize the appearance of wrinkles, treat pigmented lesions, treat vascular lesions, treat acne, treat acne scars, treat striae, or be used for a combination of the aforementioned. Partially denaturing collagen can induce and/or accelerate collagen synthesis by fibroblasts. For example, causing selective thermal injury can activate fibroblasts, which can deposit increased amounts of extracellular matrix constituents (e.g., collagen and glycosaminoglycans) that can, at least partially, rejuvenate the skin.

The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, reduce the severity of wrinkles and/or reduce discoloration of the skin. Thermal injury need not include destroying or killing tissue, cells or biomolecules. Instead, thermal injury can be confined to injury or harm while preserving the function or activity of the tissue, cells or biomolecules being treated or targeted.

In certain embodiments, thermal injury caused by the radiation can cause cell necrosis. For example, the thermal injury can cause cell necrosis in the dermis while leaving the epidermis intact for at least 3 days. The cell necrosis can occur to a depth of up to 700, 500, 300 or 200 micrometers in the dermis (although deeper or shallower injury can result).

Figure 8:
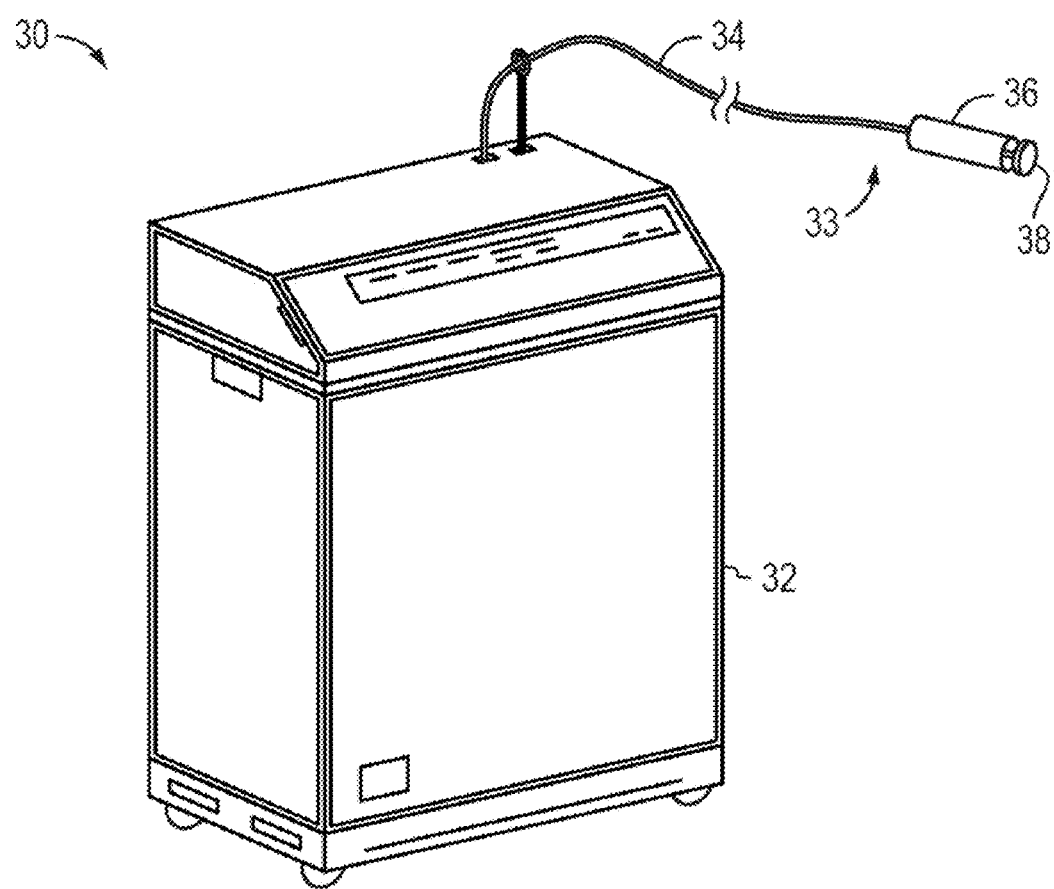
FIG. 8 is a schematic drawing of an exemplary system for treating tissue.

FIG. 8 shows an exemplary embodiment of a system 30 for treating tissue. The system 30 can be used to non-invasively deliver a beam of radiation to a target region. For example, the beam of radiation can be delivered through an external surface of skin over the target region. The system 30 includes an energy source 32 and a delivery system 33. In one embodiment, a beam of radiation provided by the energy source 32 is directed via the delivery system 33 to a target region. In the illustrated embodiment, the delivery system 33 includes a fiber 34 having a circular cross-section and a handpiece 36. A beam of radiation can be delivered by the fiber 34 to the handpiece 36, which can include an optical system (e.g., an optic or system of optics) to direct the beam of radiation to the target region. A user can hold or manipulate the handpiece 36 to irradiate the target region. The delivery system 33 can be positioned in contact with a skin surface, can be positioned adjacent a skin surface, can be positioned proximate a skin surface, can be positioned spaced from a skin surface, or a combination of the aforementioned. In the embodiment shown, the delivery system 33 includes a spacer 38 to space the delivery system 33 from the skin surface. A spacer 38 is not required however. In one embodiment, the spacer 38 can be a distance gauge, which can aid a practitioner with placement of the delivery system 33.

Referring to FIG. 8, to minimize unwanted thermal injury to tissue not targeted (e.g., an exposed surface of the target region and/or the epidermal layer), the delivery system 33 shown in FIG. 8 can include a cooling system for cooling before, during or after delivery of radiation, or a combination of the aforementioned. Cooling can include contact conduction cooling, evaporative spray cooling (using a solid, liquid, or gas), convective air flow cooling, or a combination of the aforementioned. If cooling is used, it can cool the most superficial layers of epidermal tissue. Cooling can facilitate leaving the epidermis intact.

Figure 9:
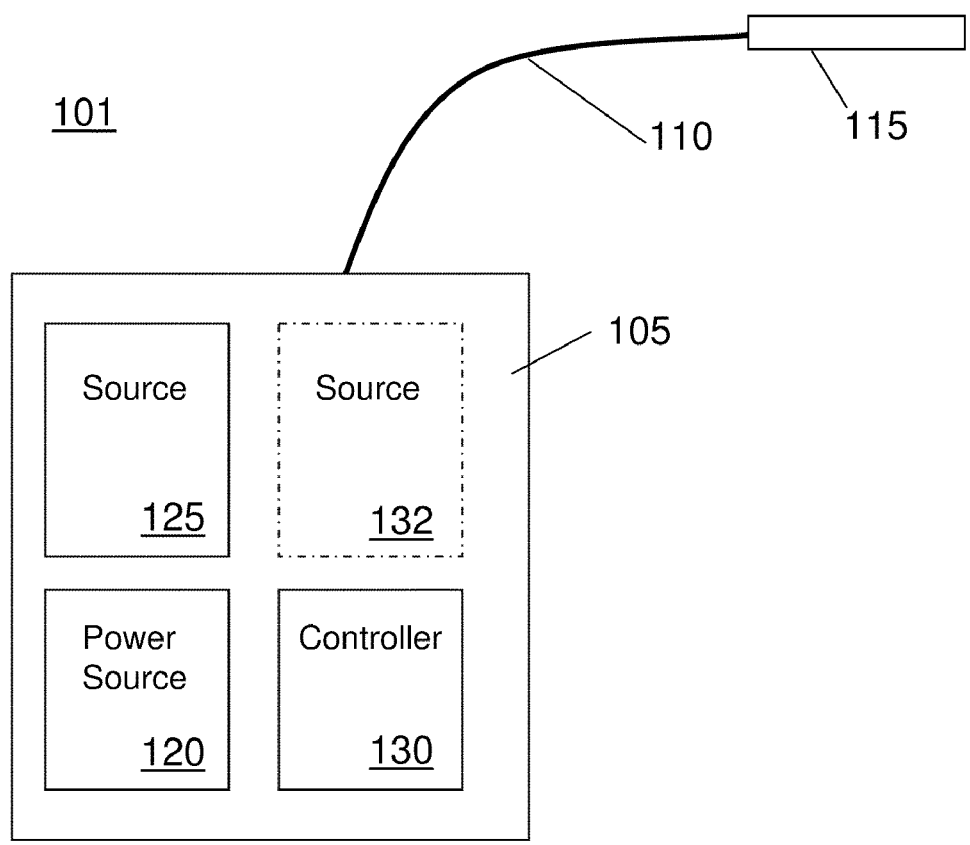
FIG. 9 shows an exemplary system that can be used to form a pattern of treatment zones in skin.

FIG. 9 shows an exemplary embodiment of a system 101 that can be used to form a pattern of treatment zones in skin. System 101 can include a base unit 105 coupled to an umbilicus 110, which is connected to a delivery module 115. The base unit 105 includes a power source 120 that supplies power to an energy source 125. The base unit 105 also includes a controller 130, which can be coupled to a user interface and can include a processing unit.

The system 101 can be used to non-invasively deliver an array of radiation beams to a target region of the skin. For example, the array of radiation beams can be delivered through an external surface of skin over the target region. In one embodiment, a beam of radiation provided by the energy source 125 is directed via the delivery module 115 to a target region. The umbilicus 110 can act as a conduit for communicating power, signal, fluid and/or gas between the base unit 105 and the delivery module 115. The umbilicus 110 can include a fiber to deliver radiation from the base unit 105 to the delivery module 115. The delivery module 115 can include an optical system (e.g., an optic or a system of optics) to convert the beam into an array of radiation beams and direct the array to the target region. The optical system can include a mask or focusing system to provide a beam of radiation having regions where no treatment radiation is delivered (e.g., to create a pattern of undamaged tissue or skin surrounded by damaged tissue or skin). A user can hold or manipulate the delivery module 115 to irradiate the target region. The delivery module 115 can be positioned in contact with a skin surface, can be positioned adjacent a skin surface, can be positioned proximate a skin surface, can be positioned spaced from a skin surface, or a combination of the aforementioned.

In certain embodiments, an array of radiation beams can be formed from a single beam of radiation by a system of optics. In various embodiments, the array of radiation beams can be formed from multiple sources. Each source can generate one beam of radiation. Multiple sources can be combined to form an array of radiation beams. In certain embodiments, multiple sources can be combined with a system of optics to form an array of radiation beams.

In certain embodiments, the base unit 105 can have a second source 132 of radiation. For example, the source 125 can provide radiation that is absorbed preferentially in the dermal skin region, and the second source 132 can provide radiation that is absorbed preferentially in the epidermal skin region.

Figure 10:
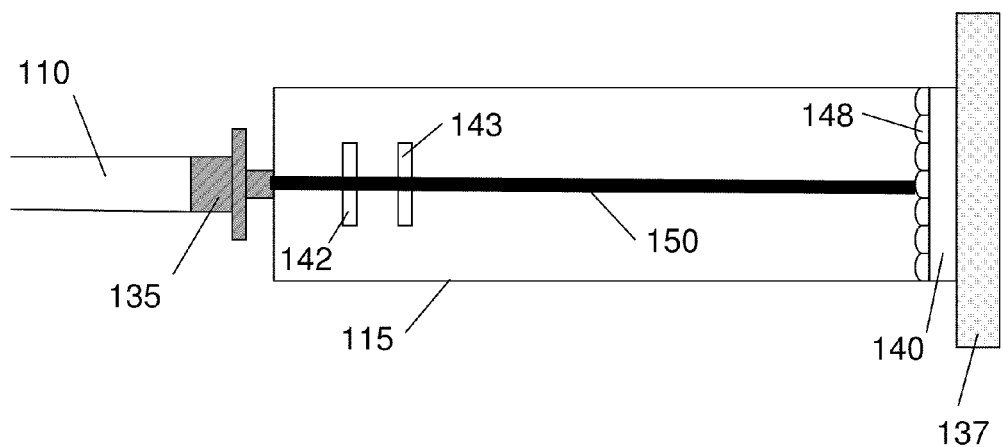
FIG. 10 shows an exemplary embodiment of a delivery module.

FIG. 10 shows an exemplary embodiment of a delivery module 115 connected to umbilicus 110 via a connector 135. In certain embodiments, connector 135 can be a coaxial RF connector such as SMA connector. The delivery module 115 includes a skin contacting portion 140 that can be brought into contact with the skin 137. The delivery module 115 includes beam steering optics 142 and 143 and optical element 148. Optics 142 and 143 can be mirrors. Optics 142 and 143 can be moved or rotated to direct the beam of radiation 150 to optical element 148. Optical element 148 can be a microlens array. The optical element 148 can be fixed, removable, or spaced from the skin contacting portion 140. In certain embodiments, the optical element 148 and skin contacting portion 140 are a single integrated unit.

Controller 130 can include a computer program and/or a mechanical device. Controller 130 can be manipulated by a user via a user interface. The user interface can include a touch screen, liquid crystal display, keypad, electrical connectors, wireless connection or a combination of the afore mentioned features. Other features and devices that are known in the art for controlling computer programs and mechanical devices can also be employed.

Controller 130 can move optical element 148 in one or more translational directions. After each translational movement, optical element 148 delivers the array of radiation beams to the skin to form a sub-pattern of injury. Each sub-pattern contributes to the overall pattern of treatment zones being formed. In certain embodiments, optical element 148 is moved in at least three translational directions before the delivery module 115 is moved to an untreated portion of the skin.

Controller 130 can move at least one of the optics 142 and 143 to move the array of radiation beams. Controller 130 can move the array in at least three translational directions before delivery module 115 is moved to an untreated portion of skin.

In this manner, a practitioner need not roll or drag delivery module 115 across or along the surface of the skin to effect a treatment. Instead, a practitioner can stamp the delivery module 115 onto the skin surface and allow the delivery module 115 to form a pattern of treatment zones before moving the delivery module 115. This allows for more uniform treatment because a practitioner's experience or hand speed need not affect the treatment.

To minimize unwanted thermal injury to tissue not targeted (e.g., an exposed surface of the target region and/or the epidermal layer), the delivery module 115 can include a cooling module for cooling before, during or after delivery of radiation, or a combination of the aforementioned. Cooling can include contact conduction cooling, evaporative spray cooling, convective air flow cooling, or a combination of the aforementioned.

The skin contacting portion 140 can include a sapphire or glass window and a fluid passage containing a cooling fluid. The cooling fluid can be a fluorocarbon type cooling fluid, which can be transparent to the radiation used. The cooling fluid can circulate through the fluid passage and past the window to cool the skin.

Figure 11:
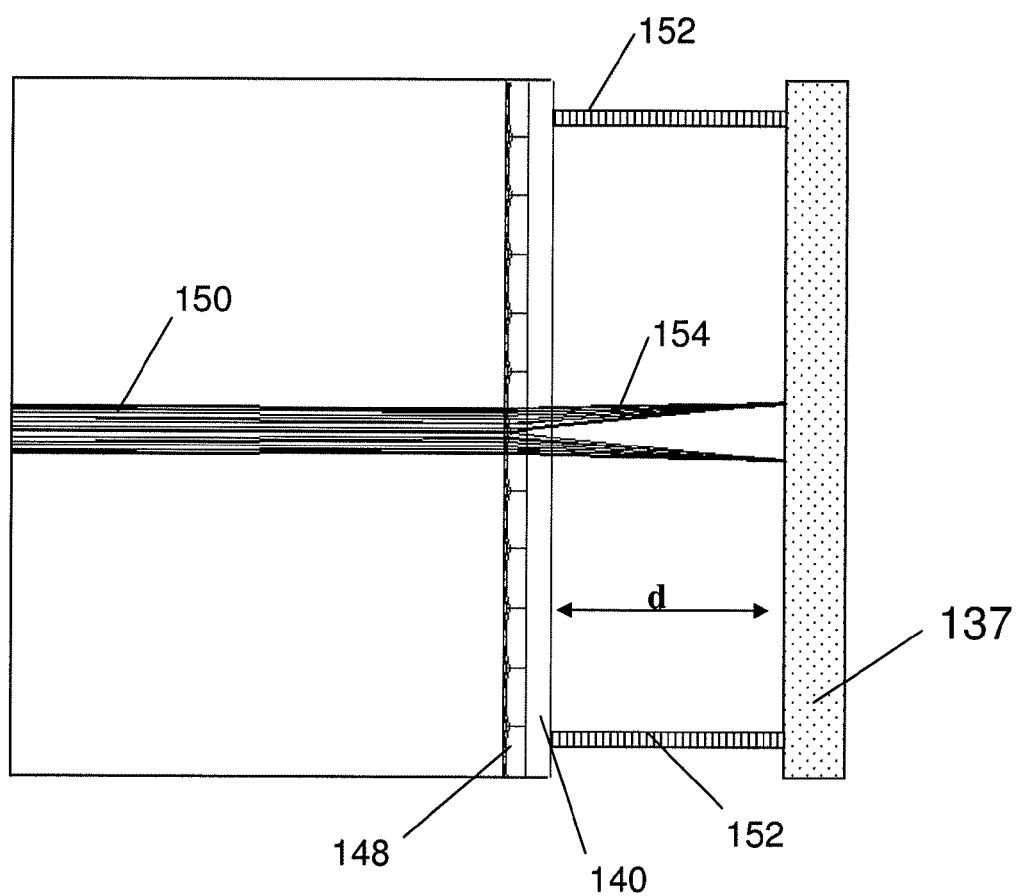
FIG. 11 shows a microlens array spaced from the skin.

As shown in FIG. 11, the delivery module 115 can include one or more spacers 152 to position the delivery module 115 relative to the skin 137. For example, the skin contacting portion 140 can be spaced from the surface of the skin 137 by a distance d. The distance d can be adjusted to control the depth of penetration of the array of radiation beams and the size of the treatment zones. In one embodiment, the spacer 152 can be a distance gauge.

In various embodiments, the energy source 32 can be an incoherent light source or a coherent light source (e.g., a laser). The energy source can be broadband or monochromatic. The beam of radiation can be a pulsed beam, a scanned beam, or a gated continuous wave (CW) beam. The laser can be a diode laser, a solid state laser, a fiber laser, a cobalt magnesium laser, or a thulium-doped laser (e.g., a crystal laser such as thulium:YAG or thulium:YAP). An incoherent source can be a light emitting diode (LED), a flashlamp (e.g., an argon or xenon lamp), an incandescent lamp (e.g., a halogen lamp), a fluorescent light source, or an intense pulsed light system. The incoherent source can include appropriate filters to block unwanted electromagnetic radiation.

In various embodiments, the beam of radiation has a wavelength of about 1890-1970 nm. The wavelength can be about 1920-1950 nm. In certain embodiments, the wavelength is about 1930 nm. In certain embodiments, the wavelength is 1930 nm. In certain embodiments, the wavelength is about 1947 nm. In certain embodiments, the wavelength is 1947 nm. A first source operating at about 1930 nm can be combined with a second source operating from about 400 nm to about 10.6 microns, can be combined with an RF source or can be combined an ultrasonic source.

In various embodiments, the beam of radiation can have a fluence of about 1 J/cm$^2$ and about 10 J/cm$^2$, for example, about 2-8 J/cm$^2$ or 3-6 J/cm$^2$. The fluence can be below about 8 J/cm$^2$, below about 6 J/cm$^2$, below about 5 J/cm$^2$, between about 3.6 to 4.9 J/cm$^2$ or between about 3.6 to 4.2 J/cm$^2$. Above the fluence, excessive damage to the skin occurs. Below the fluence, a treatment does not result in skin resurfacing. In some embodiments, the fluence is 2-6 J/cm$^2$. In certain embodiments, the fluence is 3-5 J/cm$^2$.

In various embodiments, the beam of radiation can have a spotsize between about 0.1 mm and about 30 mm, although larger and smaller spotsizes can be used depending on the application. The spotsize can be up to 30 mm, up to 25 mm, up to 20 mm, up to 15 mm, up to 10 mm, up to 5 mm, or about 3.5-4 mm. In certain embodiments, the spotsize is about 4 mm or about 20 mm.

In various embodiments, the beam of radiation can be delivered at a rate of between about 0.1 pulse per second and about 10 pulses per second, although faster and slower pulse rates can be used depending on the application.

Radiation can be applied to the skin in a stamping mode or by scanning a light source along a surface of the skin. A computerized pattern generator can be used or a handpiece can be manually manipulated to scan the light source.

In various embodiments, the parameters of the radiation can be selected to deliver the beam of radiation to a predetermined depth. In some embodiments, the beam of radiation can be delivered to the target region about 0.005 mm to about 1 mm below an exposed surface of the skin, although shallower or deeper depths can be selected depending on the application. In some embodiments, the depth is less than 0.7 mm. In some embodiments, the depth is less than 0.5 mm. In some embodiments, the depth is less than 0.3 mm. In some embodiments, the depth is less than 0.2 mm.

In various embodiments, the tissue can be heated to a temperature of between about 40° C. and about 80° C., although higher and lower temperatures can be used depending on the application. In one embodiment, the temperature is between about 55° C. and about 70° C. In one embodiment, the temperature is between about 50° C. and about 65° C.

In various embodiments, the beam of radiation can have a pulse duration between about 10 μs and about 30 s, although larger and smaller pulse durations can be used depending on the application. In certain embodiments, the beam of radiation can have a pulse duration of about 30 milliseconds to about 1 second. The pulse duration can be about 80-250 milliseconds. In certain embodiments, a longer pulse duration permits a beam of radiation to penetrate deeper into the epidermis or dermis in comparison to a beam of radiation having a shorter pulse duration, providing that all other parameters are the same.

An optical system can be used to deliver radiation to a large area beam or as a pattern of beamlets (e.g., a plurality of microbeams having a spotsize of about 0.1-2 mm) to form a pattern of thermal injury within the biological tissue.

One or more sensors can be positioned relative to a target region of skin. For example, a sensor can be positioned in contact with, spaced from, proximate to, or adjacent to the skin target. A sensor can determine a temperature on a surface of the target region, in the target region, or remote from the target region.

The sensor can be a thermistor, an array of thermistors, a thermopile, a thermocouple, a thermometer, a resistance thermometer, and a thermal-imaging based sensor, a thermographic camera, an infrared camera or any combination of the aforementioned.

A treatment apparatus can include a processor, which can be used to control the pattern generation (for delivery of radiation) and/or to correlate temperature measured by a sensor to determine the temperature in or of the target region.

The processor can generate one or more output signals to control the radiation source. For example, if the temperature in the target region reaches a threshold temperature, the processor can shut off the source to cease delivery of the radiation. The threshold temperature can be at a preset, fixed value or programmable according to user instruction. The processor can be coupled to the delivery system, can be integrated with the delivery system, or can be separate from the delivery system.

Processors suitable for the execution of computer programs include, by way of example, both general and special purpose microprocessors, and any one or more processors of any kind of digital computer. A processor can receive instructions and data from a read-only memory or a random access memory or both. A processor also includes, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

Figure 12:
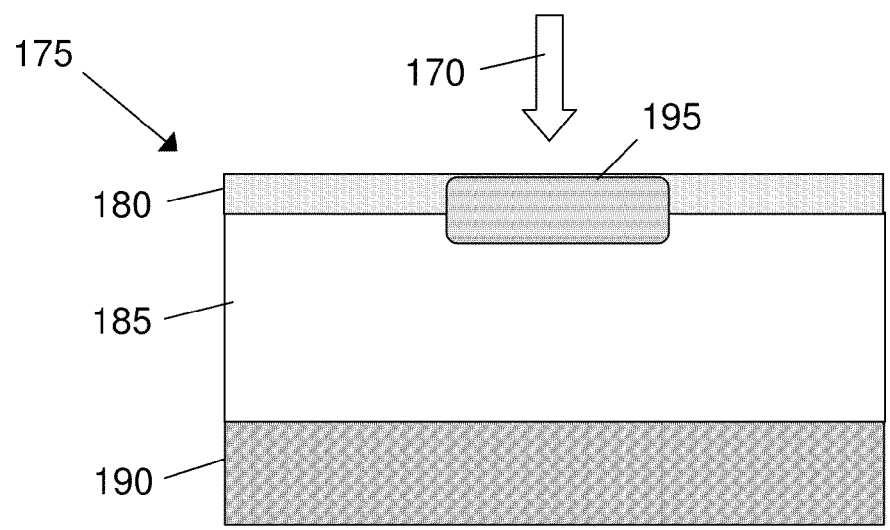
FIG. 12 shows a sectional view of a skin resurfacing treatment.

FIG. 12 shows a sectional view of an exemplary skin resurfacing treatment. The skin resurfacing can be non-ablative. Electromagnetic radiation 170 is directed to skin 175, which includes epidermis 180, dermis 185, and a subcutaneous fat region 190. The electromagnetic radiation 170 can cause thermal injury 195 to the epidermis 180 in the target region sufficient to elicit a healing response that produces a substantially improved skin condition without detachment of the epidermis 180. The thermal injury 195 can extend into the dermis 185. The thermal injury 195 can leave the epidermis 180 intact for, e.g., up to 3 days. The optical penetration depth of the electromagnetic radiation 170 can be matched to a thickness of the epidermis 180.

Figure 13:
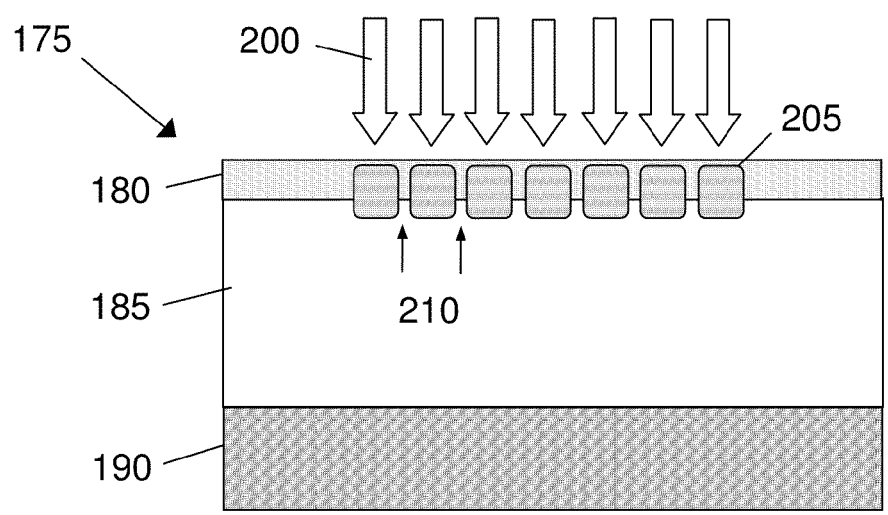
FIG. 13 shows a sectional view of another skin resurfacing treatment.

FIG. 13 shows a sectional view of another exemplary skin resurfacing treatment. The skin resurfacing can be non-ablative. Electromagnetic radiation 200 is directed to skin 175, which includes epidermis 180, dermis 185, and a subcutaneous fat region 190. The electromagnetic radiation 200 can include an array of radiation beams delivered to the skin 175 to a plurality of treatment zones 205. The electromagnetic radiation 170 can cause thermal injury 205 to the epidermis 180 in the target region sufficient to elicit a healing response that produces a substantially improved skin condition without detachment of the epidermis 180. The thermal injury 205 can extend into the dermis 185. The thermal injury 205 can leave the epidermis 180 intact for, e.g., up to 3 days. The optical penetration depth of the electromagnetic radiation 200 can be matched to a thickness of the epidermis 180. Each treatment zone or thermal injury 205 can be separated by substantially undamaged skin 210. Healing can initiate from less injured or substantially undamaged skin 210 adjacent the plurality of treatment zones.

Figure 14:
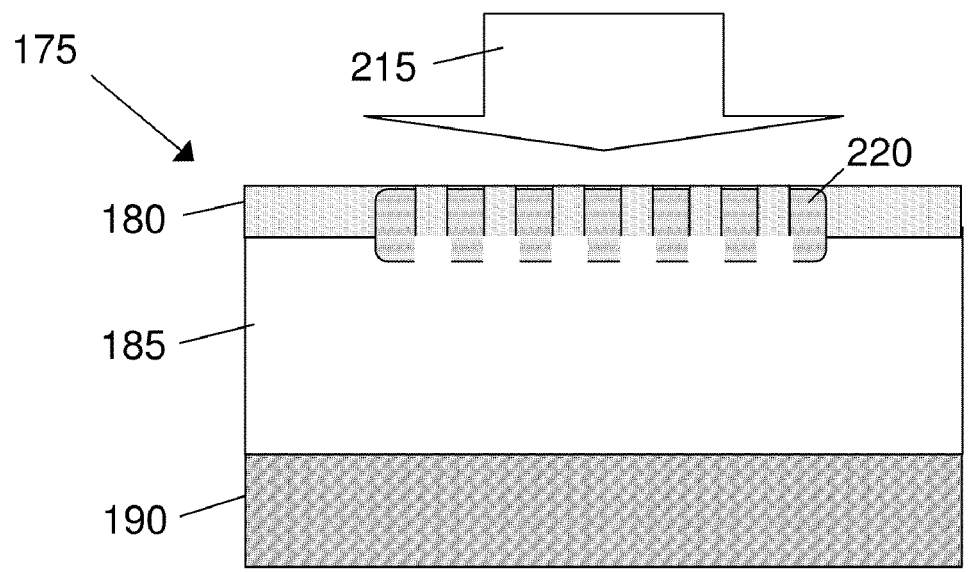
FIG. 14 shows a sectional view of another skin resurfacing treatment.

FIG. 14 shows a sectional view of another exemplary skin resurfacing treatment. The skin resurfacing can be non-ablative. Electromagnetic radiation 215 is directed to skin 175, which includes epidermis 180, dermis 185, and a subcutaneous fat region 190. The electromagnetic radiation 215 can cause thermal injury 220 to the epidermis 180 in the target region sufficient to elicit a healing response that produces a substantially improved skin condition without detachment of the epidermis 180. The thermal injury 220 can extend into the dermis 185. The thermal injury 220 can leave the epidermis 180 intact for, e.g., up to 3 days. The optical penetration depth of the electromagnetic radiation 215 can be matched to a thickness of the epidermis 180.

Figure 15:
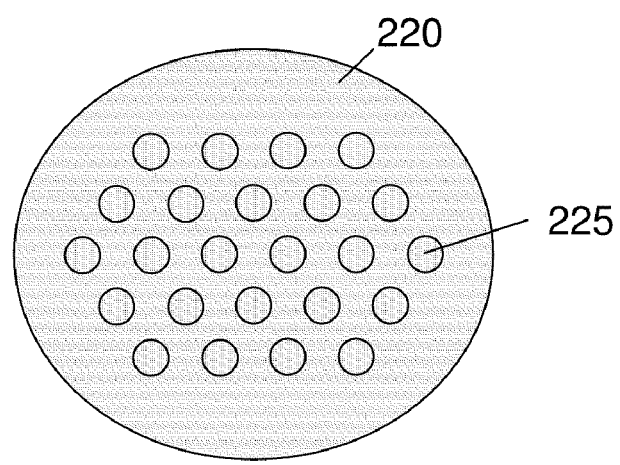
FIG. 15 shows a top view of the thermal injury caused by the skin resurfacing treatment shown in FIG. 14.

FIG. 15 shows a top view of the thermal injury 220 caused by the skin resurfacing treatment shown in FIG. 14. Treatment zone 220 surrounds regions of untreated epidermis 225 forming islands of undamaged or untreated tissue, or undamaged or untreated tissue surrounded by substantially damaged or treated tissue.

Figure 16:
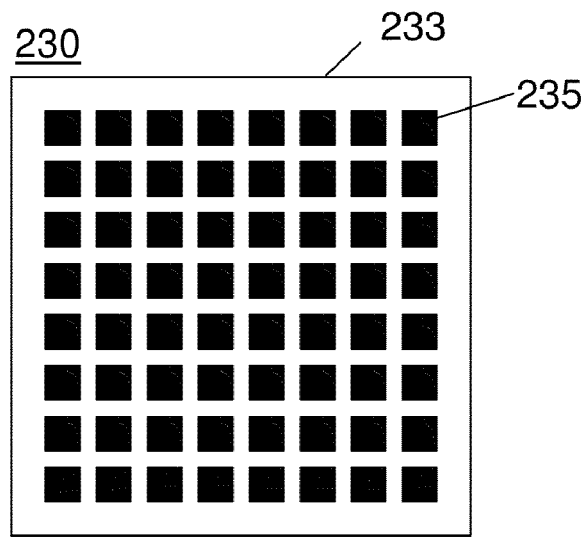
FIG. 16 shows an exemplary mask for forming a reverse fractional pattern.

FIG. 16 shows an exemplary mask 230 for forming a beam of radiation into a patterned beam capable of forming a reverse fractional pattern, or a pattern of undamaged tissue or skin surrounded by damaged tissue or skin. The mask 230 includes a substrate 233 including a coating 235. The substrate 233 can be fused silica, quartz, sapphire, or infraseal. The coating 235 can be a dialectic and/or anti-reflective coating. The coating 235 can be a filter or mirrored coating. The coating 235 can be reflective, opaque or translucent. The regions between the coating 235 can be uncoated or include a clear, transmitting coating.

The beam of radiation incident on the mask 230 can be collimated, convergent or divergent. The coating 235 can block the radiation at the coated portions, and allow radiation to be transmitted through the uncoated portions of the substrate 233. In certain embodiments, the coating is not disposed on an outer surface of the substrate 233, and is instead disposed inside the substrate. The coating 235 can be integrally formed on or inside the substrate 233, and can be formed inside the substrate by imaging the coated masked portions in the substrate or sandwiching the coating between two substrates.

Although the coating 235 is shown as squares, circular or any polygonal shape (e.g., triangular, rectangular, pentagonal, hexagonal, or octagonal) can be used. Likewise, the substrate 233 can be circular or any polygonal shape (e.g., triangular, rectangular, pentagonal, hexagonal, or octagonal). The shape of the substrate 233 and the coating 235 need not match.

The substrate 233 can be about 15 mm×15 mm. The coating 235 can be about 0.5 mm to about 2 mm thick. In certain embodiments, the coating 235 is about 1 mm.

The coated regions 235 can be 0.5 mm to about 5 mm in cross-section or diameter. For example, the coated regions 235 can be 0.75, 1, 1.5, or 2 mm in cross-section or diameter. In detailed embodiment, the coated regions 235 is about 1 mm.

The distance between the coated regions 235 can be 100 micrometers to about 2 mm. The distance between the coated regions 235 can be about 200, 250, 500, 600, 700, 750, 1000, 1,250, or 1,500 micrometers. In one detailed embodiment, the distance between the coated regions 235 is about 500 micrometers. In one detailed embodiment, the distance between the coated regions 235 is about 700 micrometers.

The substrate 233 can be placed directly on the skin, adjacent to the skin, or spaced from the skin. The substrate 233 can be cooled or include a cooling element between it and the skin.

Figure 17:
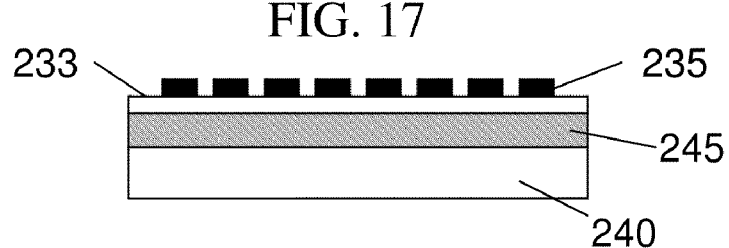
FIG. 17 shows a sectional view of a mask 230 for forming a reverse fractional pattern.

FIG. 17 shows a sectional view of a mask 230 mounted on a cooling substrate 240. A space 245 between the mask 230 and the cooling substrate 240 can pass a cooling fluid (e.g., a cryogenic liquid, fluorinert, a cooling gas, a cooling liquid, or water) across cooling substrate 240.

Figure 18:
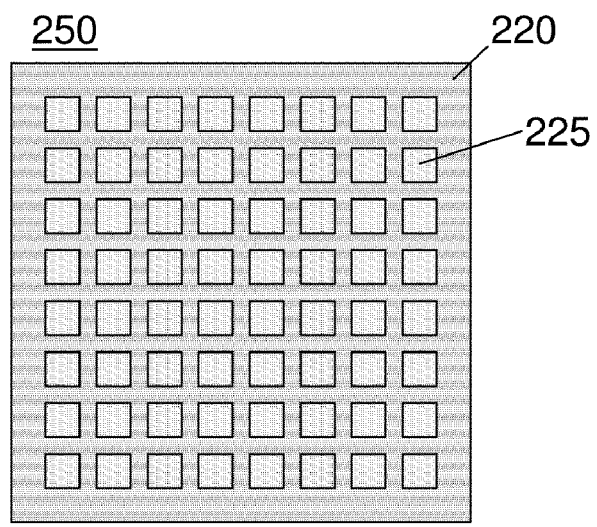
FIG. 18 shows an exemplary pattern of damage including untreated zones surrounded by a treatment region.

FIG. 18 shows an exemplary pattern 250 of damage including untreated zones 225 surrounded by a treatment region 220. The untreated zones 225 correspond to a respective coated region 235. The treatment region 220 can form lines of damage in the skin. The pattern 250 can promote contraction of the skin in the treatment region 220 (e.g., by coagulation), which results in pulling or stretching of the skin in the untreated zones 225. As a result, the region of skin being treated can be resurfaced, tightened, or made less lax. Collagen remodeling can also occur in the treatment region 220.

While the invention has been particularly shown and described with reference to specific illustrative embodiments, it should be understood that various changes in form and detail may be made without departing from the spirit and scope of the invention.

What is claimed is:

1. A method of non-ablative skin resurfacing, comprising:
generating electromagnetic radiation having a wavelength of about 1920 nm to about 1950 nm and a fluence of about 3 J/cm$^2$ to about 6 J/cm$^2$;
delivering the electromagnetic radiation to a target region of skin; and
causing thermal injury to an epidermis in the target region sufficient to elicit a healing response that produces a substantially improved skin condition without detachment of the epidermis.

2. The method of claim 1 further comprising causing thermal injury while leaving the epidermis intact for up to 3 days.

3. The method of claim 1 further comprising causing thermal injury while leaving the epidermis intact for up to 7 days.

4. The method of claim 1 further comprising causing thermal injury to an upper portion of a dermis in the target region of skin.

5. The method of claim 1 further comprising causing cell necrosis to a depth of up to 300 micrometers in a dermis while leaving the epidermis intact for at least 3 days.

6. The method of claim 1 further comprising causing thermal injury without acute cosmetic disturbance to the epidermis.

7. The method of claim 1 further comprising matching optical penetration depth of the electromagnetic radiation to a thickness of the epidermis.

8. The method of claim 1 further comprising exposing the target region of skin to the electromagnetic radiation for up to 1 second.

9. The method of claim 1 wherein the wavelength of the electromagnetic radiation is about 1930 nm.

10. The method of claim 1 wherein the wavelength of the electromagnetic radiation is about 1947 nm.

11. The method of claim 1 further comprising generating the electromagnetic radiation using a pulsed source.

12. The method of claim 1 further comprising generating the electromagnetic radiation using at least one of scanned or gated continuous wave source.

13. The method of claim 1 further comprising forming a plurality of thermal injuries, each thermal injury separated from adjacent thermal injuries by substantially undamaged epidermal tissue.

14. The method of claim 1 further comprising forming a pattern of thermal injuries in the target region of skin.

15. The method of claim 1 further comprising forming a reverse fractional pattern including regions of undamaged tissue surrounded by damaged tissue.

16. The method of claim 1 further comprising using a thulium-doped laser to generate the electromagnetic radiation.

17. The method of claim 1 further comprising using a thulium:YAP laser to generate the electromagnetic radiation.

18. A method of non-ablative skin resurfacing, comprising:
generating electromagnetic radiation having a wavelength of about 1920 nm to about 1950 nm and a fluence of about 3 J/cm$^2$ to about 6 J/cm$^2$;
delivering the electromagnetic radiation to a target region of skin including an epidermis and a dermis; and
causing thermal injury to the epidermis and to the dermis in the target region sufficient to elicit a healing response that produces a substantially improved skin condition without detachment of the epidermis.

19. The method of claim 18 further comprising causing cell necrosis to a depth of up to 300 micrometers in the dermis while leaving the epidermis intact for at least 3 days.

20. The method of claim 18 further comprising matching optical penetration depth of the electromagnetic radiation to a thickness of the epidermis.

21. The method of claim 18 further comprising exposing the target region of skin to the electromagnetic radiation for up to 1 second.

22. The method of claim 16 wherein the wavelength of the electromagnetic radiation is about 1930 nm.

23. A method of non-ablative skin resurfacing, comprising:
generating electromagnetic radiation having a wavelength of about 1930 nm and a fluence of up to 5 J/cm$^2$;
delivering the electromagnetic radiation to a target region of skin; and
causing thermal injury to the epidermis in the target region sufficient to elicit a healing response that produces a substantially improved skin condition without detachment of the epidermis.

24. A method of non-ablative skin resurfacing, comprising:
generating electromagnetic radiation having a wavelength of about 1920 nm to about 1950 nm, a fluence of about 3 J/cm$^2$ to about 6 J/cm$^2$, and a pulse duration up to 1 second;
delivering the electromagnetic radiation to a target region of skin; and
causing thermal injury to the epidermis in the target region sufficient to elicit a healing response that produces a substantially improved skin condition without detachment of the epidermis.

25. The method of claim 24 further comprising causing cell necrosis to a depth of up to 300 micrometers in the dermis leaving the epidermis intact for at least 3 days.

26. The method of claim 24 wherein the pulse duration is less than or equal to 250 milliseconds.

27. The method of claim 24 further comprising using a thulium doped laser to generate the electromagnetic radiation.

28. The method of claim 24 further comprising using a diode laser to generate the electromagnetic radiation.

29. The method of claim 24 further comprising:
causing cell necrosis to a depth of up to 300 micrometers in the dermis; and
reducing the appearance of wrinkles.

* * * * *

UNITED STATES PATENT AND TRADEMARK OFFICE
CERTIFICATE OF CORRECTION

| | | |
|---|---|---|
| PATENT NO. | : 8,328,795 B2 | Page 1 of 1 |
| APPLICATION NO. | : 12/754374 | |
| DATED | : December 11, 2012 | |
| INVENTOR(S) | : Domankevitz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 339 days.

Signed and Sealed this
Twenty-eighth Day of May, 2013

Teresa Stanek Rea
*Acting Director of the United States Patent and Trademark Office*